(12) United States Patent
Hauer et al.

(10) Patent No.: US 7,553,648 B2
(45) Date of Patent: Jun. 30, 2009

(54) CYTOCHROME P450 MONOOXYGENASES CONSISTING OF THERMOPHILIC BACTERIA

(75) Inventors: Bernhard Hauer, Fußgönheim (DE); Rolf Schmid, Stuttgart (DE); Rainer Merkl, Bovenden (DE); Francesca Blasco, Esslingen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 621 days.

(21) Appl. No.: 10/398,178

(22) PCT Filed: Oct. 16, 2001

(86) PCT No.: PCT/EP01/11958

§ 371 (c)(1),
(2), (4) Date: Apr. 2, 2003

(87) PCT Pub. No.: WO02/33057

PCT Pub. Date: Apr. 25, 2002

(65) Prior Publication Data

US 2005/0048484 A1    Mar. 3, 2005

(30) Foreign Application Priority Data

Oct. 16, 2000    (DE) ................. 100 51 175

(51) Int. Cl.
| | |
|---|---|
| *C12N 9/02* | (2006.01) |
| *C12N 15/00* | (2006.01) |
| *C12N 1/20* | (2006.01) |
| *C12P 7/00* | (2006.01) |
| *C12P 21/04* | (2006.01) |
| *C12Q 1/00* | (2006.01) |
| *C07H 21/04* | (2006.01) |
| *C12Q 1/68* | (2006.01) |

(52) U.S. Cl. ................. 435/189; 435/4; 435/6; 435/440; 435/252.3; 435/320.1; 435/69.1; 435/71.1; 435/132; 536/23.2

(58) Field of Classification Search ............ 435/189, 435/25, 69.1, 71.1, 440, 131, 252.3, 320.1, 435/4, 6, 18; 536/23.2, 23.7, 23.1
See application file for complete search history.

(56) References Cited

FOREIGN PATENT DOCUMENTS

| | | |
|---|---|---|
| CA | 2379518 | 1/2001 |
| CA | 2378615 | 2/2001 |
| CA | 2380186 | 2/2001 |

OTHER PUBLICATIONS

Zamorano et al., GenBank accession No. CAB77247, Oct. 2000.*
Henne et al. The genome sequence of the extreme thermophile Thermus thermophilus. Nat. Biotechnol. 22:547-553(2004).*
Ruettinger et al. Coding nucleotide, 5' regulatory, and deduced amino acid sequences of P-450BM-3, a single peptide cytochrome P-450:NADPH-P-450 reductase from *Bacillus megaterium*. J. Biol. Chem. 264 (19), 10987-10995 (1989).*
Branden et al. Introduction to Protein Structure, Garland Publishing Inc., New York, p. 247, 1991.*
Guo et al. Proc Natl Acad Sci USA. Jun. 22, 2004;101(25):9205-10.*

* cited by examiner

*Primary Examiner*—Yong D Pak
(74) *Attorney, Agent, or Firm*—Novak Druce + Quigg LLP

(57) ABSTRACT

The invention relates to novel cytochrome P450 monooxygenases from thermophilic bacteria, in particular the genus *Thermus* sp., to nucleotide sequences encoding them, to the recombinant production of these monooxygenases and to their use for the microbiological oxidation of organic compounds.

5 Claims, 2 Drawing Sheets

Fig. 1

Figure 2:
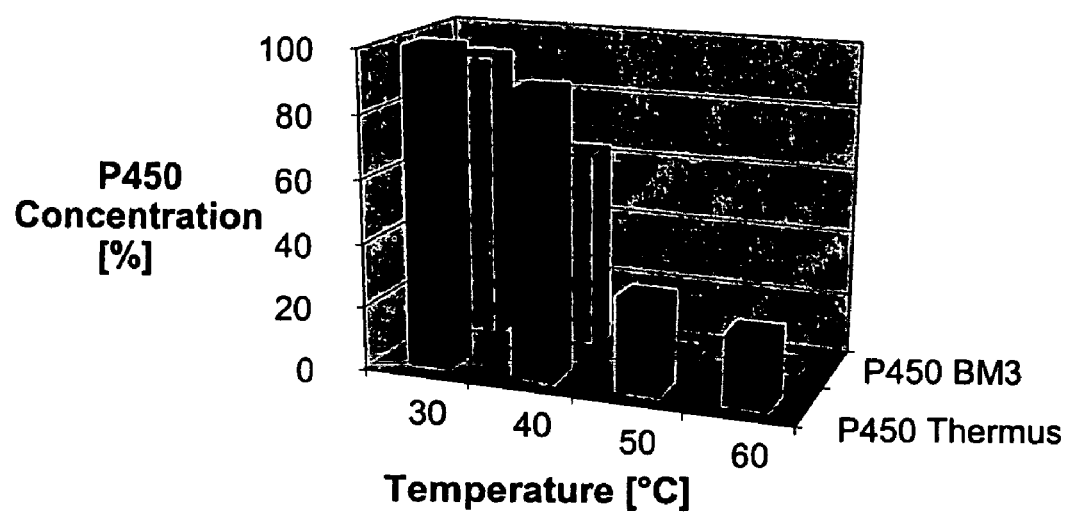

```
P450 BM3       TIKEMPQPKTFGELKNLPLLNTDKPVQALMKIADELGEIFKFEAPGRVTRYLSSQRLIKE  60
P450 thermus   -MKRLSLREAWPYLKDLQQD----PLAVLLAWGRAHPRLFLPLPRFPLALIFDPE-GVEG  54
               :*.:. ::: **:*        *: .*:  . ..:*   .  :: :..: ::

P450 BM3       ACDESRFDKNLSQALKFVRDFAGDGLFTSWTHEKNWKKAHNILLPSFSQQAMKGYHAMMV 120
P450 thermus   ALLAEGTTKATFQYRALSR-LTGRGLLTDWG--ESWKEARKALKDPFLPKNVRGYREAME 111
               *  .  *   *    : * ::*  **:*.*  :.**:*::  * .*  :  ::**: *

P450 BM3       DIAVQLVQKWERLNADEHIEVPEDMTRLTLDTIGLCGFNYRFNSFYRDQPHPFITSMVRA 180
P450 thermus   EEARAFFGEWR----GEERDLDHEMLALSLRLLGRALFGKPLSPSLAEH-------ALKA 160
               : *  :. :*.    .*. :: ..:* *:* :* . *. :..   ::       ::*

P450 BM3       LDEAMNKLQRANPDDPAYDENKRQFQEDIKVMNDLVDKIIADRKASGEQSDDLLTHMLNG 240
P450 thermus   LDRIMAQTR--SPLALLDLAAEARFR-----------K--DRGALYREAEALIVHPPLS 204
               **. * : :  .*        : :*:           ** *  .::: *:.*    .

P450 BM3       KDPETGEPLDDENIRYQIITFLIAGHETTSGLLSFALYFLVKNPHVLQKAAEEEAARVLVD 300
P450 thermus   HLP-------RERALSEAVTLLVAGHETVASALTWSFLLLSHRPDWQKRVAESEEAALAA 257
               : *       *.  : :*:*:***** .. *:::: :*  .*. ::.**.    .*.

P450 BM3       PVPSYKQVKQLKYVGMVLNEALRLWPTAPAFSLYAKEDTVLGGEYPLEKGDELMVLIPQL 360
P450 thermus   ---------------FQEALRLYPPAWILTRRLERPLLLG-EDRLPPG-TTLVLSPYV 298
                              ::*****:*.*  ::   :. :** *   :** * :

P450 BM3       HRDKTIWGDDVEEFRPERFENPSAIPQHAFKPFGNGQRACIGQQFALHEATLVLGMMLKH 420
P450 thermus   TQRLHFP--DGEAFRPERFLEERGTPSGRYFPFGLGQRLCLGRDFALLEGPIVLRAFFRR 356
               : :   * * *****::  . *. :  . :***  ***  *:*:*** *   :*   ::::

P450 BM3       FDFEDHTNYELDIKETLTLKPEGFVVKAKSKKIPLGGIPS-PSTEQSAKKVR 471 (SEQ ID NO:11)
P450 thermus   FRLDPLP--FPRVLAQVTLRPE-------------GGLPARPREEVRA---- 389 (SEQ ID NO:2)
               * ::  .   :  :**:**       **:*: *  *  *
```

CYTOCHROME P450 MONOOXYGENASES CONSISTING OF THERMOPHILIC BACTERIA

The invention relates to novel cytochrome P450 monooxygenases from thermophilic bacteria, in particular from the genus *Thermus* sp., to nucleotide sequences encoding them, to the recombinant preparation of these monooxygenases, and to their use for the microbiological oxidation of organic compounds.

Cytochrome P450 monooxygenases have the ability of catalyzing oxygenation reactions which are of industrial interest and have therefore been researched intensively for some time. Thus, for example, the cytochrome P450 monooxygenase BM-3 has been isolated from *Bacillus megaterium* and characterized and can now be obtained by the recombinant route (cf., for example, DE-A-199 35 115).

This cytochrome P450-monooxygenase usually catalyzes the subterminal hydroxylation of long-chain, saturated acids and of the corresponding amides and alcohols thereof or the epoxidation of unsaturated long-chain fatty acids or saturated fatty acids with medium chain length. The optimal chain length of saturated fatty acids is 14 to 16 carbon atoms.

The structure of the heme domain of P450 BM-3 was determined by X-ray structural analysis. The substrate binding site is in the form of a long tunnel-like opening which reaches from the surface of the molecule to the heme molecule and is delimited virtually exclusively by hydrophobic amino acid residues. The only charged residues at the surface of the heme domain are the residues Arg47 and Tyr51. It is assumed that the latter participate in the binding of the carboxylate group of the substrate by forming a hydrogen bond. In the meantime, the substrate spectrum of this enzyme has been widened successfully by the targeted introduction of point mutations. Thus, the oxidation of both shorter- and longer-chain carboxylic acids, alkanes, alkenes, cycloalkanes, cycloalkenes and a wide range of aromatics by this enzyme is now possible (cf. DE-A-199 35 115, 199 55 605, 100 11 723 and 100 14 085).

To improve the industrial applicability of this class of enzymes further, it would therefore be desirable to find novel cytochrome P450 monooxygenases which are better adapted to industrial production conditions, such as, for example, enzymes with increased thermal stability.

The object of the present invention was therefore to provide cytochrome P450 monooxygenases which are adapted better to industrial production conditions.

The above object was achieved by providing a cytochrome P450 monooxygenase which comprises an amino acid sequence encompassing a subsequence from the amino acid residue Pro328 to Glu345 in accordance with SEQ ID NO:2 and preferably also a subsequence from the amino acid residue Val216 to Ala227 in accordance with SEQ ID NO:2.

Cytochrome P450 monooxygenases which are preferred in accordance with the invention have an amino acid sequence encompassing at least one further subsequence which is selected from among a subsequence of at least 10 successive amino acids from the sequence regions predetermined by the amino acid residues Met1 to Phe327 and Gly346 to Ala389 in accordance with SEQ ID NO:2.

An especially preferred cytochrome P450 monooxygenase has an amino acid sequence which corresponds essentially to SEQ ID NO: 2.

Cytochrome P450 monooxygenases according to the invention can be isolated in particular from thermophilic bacteria, preferably of the genus *Thermus* sp., such as, for example, the species *Thermus thermophilus*, strain HB27 (deposited at the DSM under Number DSM7039). In accordance with the invention, "Thermophilic" bacteria meet the temperature tolerance criteria of H. G. Schlegel, Allgemeine Mikrobiologie [General Microbiology], Thieme Verlag Stuttgart, 5th Edition, page 173, for thermophiles and extreme thermophiles (i.e. growth optimum at over 40° C.).

The monooxygenases according to the invention are preferably characterized by an increased thermostability. This takes the form of a lower loss of activity at elevated temperature compared to the *Bacillus megaterium* P450 BM-3 (for example in a range of from 30 to 60° C., pH 7.5, 25 mM Tris/HCl).

In accordance with a preferred embodiment, a cytochrome P450 monooxygenase is provided in accordance with the invention from the thermophilic bacterium *T. thermophilus*. The protein has a molecular weight of approximately 44 kDa (determined by SDS gel electrophoresis), is soluble, and has an absorption spectrum in the reduced state, oxidized state, and as carbonyl adduct which is analogous to that of the other P450 enzyme. The following identities were determined from sequence alignments of this enzyme according to the invention from *T. thermophylus* and other known P450 enzymes: P450 BM3, 32% identity; CYP119, 29% identity; P450eryF, 31% identity. The enzyme according to the invention has extraordinary thermostability, which is demonstrated by a melting temperature of approximately 85° C., which value is 30° C. above that of P450cam.

The subject matter of the invention are furthermore oligonucleotides which hybridize with a nucleic acid sequence encoding a cytochrome P450 monooxygenase according to the invention.

In particular, the subject matter of the invention are also those oligonucleotides which encompass a nucleic acid sequence which is essentially complementary to a nucleotide sequence region in accordance with SEQ ID NO:1 which encompasses at least 30 to 45 successive nucleotide residues.

A further subject matter of the invention relates to polynucleotides which hybridize with an oligonucleotide as defined above and which encode a cytochrome P450 monooxygenase, in particular a cytochrome P450 monooxygenase from other microorganisms, such as, for example, those of the genus *Thermus* sp.

The subject matter of the present invention are, in particular, also polynucleotides which encode a cytochrome P450 monooxygenase as defined above, and polynucleotides which are complementary thereto.

Preferred polynucleotides are those which have essentially a nucleic acid sequence in accordance with SEQ ID NO: 1, and the nucleic acid sequences which are complementary thereto and derived therefrom.

A further subject matter of the invention relates to expression cassettes for the recombinant production of monooxygenases according to the invention, comprising at least one regulatory nucleic acid sequence linked operably to at least one of the polynucleotides stated above.

Further subject matters of the invention relate to recombinant vectors which carry at least one polynucleotide or at least one expression cassette as defined above; and to microorganisms comprising at least one such recombinant vector; and to processes for the preparation of cytochrome P450 monooxygenases according to the invention, in which a microorganism which produces cytochrome P450 monooxygenase is cultured and the monooxygenase is isolated from the culture.

The enzymes according to the invention and mutants which can be derived therefrom are useful as biocatalysts for various biochemical oxygenation reactions of organic compounds of industrial importance. Analogously, the recombinant microorganisms according to the invention can also be employed for carrying out such oxygenation reactions.

A further subject matter of the invention therefore relates to a process for the microbiological oxidation of an organic compound, wherein this compound is reacted with at least one cytochrome P450 monooxygenase according to the invention.

This process is preferably carried out in such a way that a1) a recombinant microorganism as defined above is cultured in a culture medium in the presence of the exogenous (externally supplied) organic compound, or the organic compound which has been formed as intermediate, which compound is a substrate for monooxygenase, preferably in the presence of oxygen and if appropriate an electron donor; or a2) a substrate-containing reaction medium is incubated with a cytochrome P450 monooxygenase according to the invention, preferably in the presence of oxygen and an electron donor; and b) the oxidation product formed or a subsequent product thereof is isolated from the medium.

The exogenous substrate, or the substrate which has been formed as intermediate, can be selected from among:

a) optionally substituted N-, O- or S-heterocyclic mono-, di- or polynuclear aromatic compounds;

b) optionally substituted mono- or polynuclear aromatics;

c) straight-chain or branched alkanes and alkenes;

d) optionally substituted cycloalkanes and cycloalkenes; and e) aliphatic, preferably terminally saturated, carboxylic acids.

In a first preferred variant of the process according to the invention, the oxidation is carried out by culturing the microorganisms in the presence of oxygen at a culture temperature of at least approximately 20° C. and a pH of approximately 6 to 9.

In a second preferred variant of the process according to the invention, at least one compound selected from among the above-defined groups a) to e) is added as exogenous substrate to a medium and the oxidation is carried out by enzymatic conversion of the substrate-containing medium in the presence of oxygen at a temperature of at least approximately 20° C. and a pH of approximately 6 to 9, wherein the substrate-containing medium additionally contains an approximately 10- to 100-fold molar excess of reduction equivalents (electron donor) based on the substrate.

The above processes can preferably be carried out in bioreactors. The subject matter of the invention are therefore such bioreactors, comprising at least one monooxygenase according to the invention or at least one recombinant microorganism, if appropriate in each case in immobilized form.

Finally, the invention relates to the use of a cytochrome P450 monooxygenase, of a vector or a microorganism according to the present invention for the microbiological oxidation of the abovementioned classes of organic compounds.

The invention is now illustrated in greater detail with reference to the appended figures. In these figures, FIG. 1 shows a P450 *Thermus thermophilus* with the heme domain of *Bacillus megaterium* P450 BM3. The heme binding site is shown doubly underlined (Cys400 in P450 BM3 is the cystein residue which coordinates with the iron atom of the prosthetic group). The region which is in contact with the ω-end of the fatty acid chain is singly underlined. The extent of their agreement is designated by different symbols ("*"=identical residues; ":" and "."=similar residues).

FIG. 2 shows the result of a comparison test for determining the thermostability of P450 BM3 and *Thermus* sp. P450. The thermostability was determined spectrometrically in a wavelength range between 400 and 500 nm over the heme group content.

Also encompassed in accordance with the invention are "functional equivalents" of the new P450 monooxygenases which have been disclosed specifically.

"Functional equivalents" or analogs of the monooxygenases which have been disclosed specifically are, for the purposes of the present invention, enzymes which differ from the above and which continue to show the desired substrate specificity within the scope of at least one of the above-designated oxidation reactions a) to e) and/or show an increased thermostability in comparison with P450 BM3, for example at temperatures in the range of approximately 30 to 60° C. and, if appropriate, higher temperatures after treatment for 30 minutes in 25 mM Tris/HCl.

"Functional equivalents" are understood as meaning in accordance with the invention in particular mutants which exhibit an amino acid other than the amino acid mentioned specifically in at least one of the abovementioned sequence positions but which still catalyze one of the abovementioned oxidation reactions. "Functional equivalents" thus also encompass the mutants which are obtainable by one or more, such as for example 1 to 30 or 1 to 20 or 1 to 10, amino acid additions, substitutions, deletions and/or inversions, it being possible for the abovementioned modifications to occur in any sequence position as long as they lead to a mutant with the spectrum of properties according to the invention. Functional equivalence exists in particular also when the reactivity patterns between mutant and unmodified enzyme agree in terms of quality, i.e. when identical substrates are converted at different rates.

"Functional equivalents" also encompassed in accordance with the invention have an amino acid sequence which differs from SEQ ID NO:2 in at least one position, the modification in the sequence modifying the monooxygenase activity preferably only inconsiderably, i.e. by not more than approximately ±90%, in particular ±50% or not more than ±30%. This modification can be determined using a reference substrate, such as, for example, β-ionone, under standardized conditions (for example 0.1 to 0.5M substrate, pH range 6 to 8, in particular 7; T=60 to 70° C., in particular 65° C.).

"Functional equivalents" also encompassed in accordance with the invention are homologs to the specifically disclosed proteins. They have at least 60% homology, preferably at least 75% homology, in particular at least 85% homology, such as, for example, 90%, 95% or 99%, homology with one of the specifically disclosed sequences, calculated by the algorithm of Pearson and Lipman, Proc. Natl. Acad. Sci. (USA) 85(8), 1988, 2444-2448.

Homologs of the proteins or polypeptides according to the invention can be generated by mutagenesis, for example by point mutation or truncation of the proteins.

Homologs of the protein according to the invention can be identified by screening combinatory libraries of mutants, such as, for example, truncated mutants. For example, a variegated library of protein variants can be generated by combinatory mutagenesis at the nucleic acid level, such as, for example, by the enzymatic ligation of a mixture of synthetic oligonucleotides. There exists a multiplicity of processes which can be used for generating libraries of potential homologs from a degenerate oligonucleotide sequence. The chemical synthesis of a degenerate gene sequence can be carried out in a DNA synthesizer, and the synthetic gene can be ligated into a suitable expression vector. The use of a degenerate set of genes makes it possible to provide, in a mixture, all sequences which encode the desired set of potential protein sequences. Methods for the synthesis of degenerate oligonucleotides are known to the skilled worker (for example Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:447).

"Functional equivalents" naturally also encompass P450 monooxygenases which can be obtained from other organisms, for example from other bacteria than those mentioned specifically herein, and naturally occurring variants. For example, areas of homologous sequence regions can be identified by sequence alignment and equivalent enzymes can be determined with reference to the specific objects of the invention.

The substrates of group a) which can be oxidized in accordance with the invention are optionally substituted heterocyclic mono-, bi- or polynuclear aromatic compounds; in particular N-, O- or S-heterocyclic mono-, bi- or polynuclear aromatic compounds which can be oxidized or hydroxylated. They encompass for example two or three four- to seven-membered, in particular six- or five-membered, fused rings where at least one, preferably all, of the rings have the aromatic character and where at least one of the aromatic rings has one to three, preferably one, N-, O- or S-hetero atom attached to the ring. If appropriate, the entire ring structure may contain one or two further identical or different hetero atoms. Furthermore, the aromatic compounds can have 1 to 5 substituents attached to the ring carbon atoms or to the hetero atoms. Examples of suitable substituents are $C_1$- to $C_4$-alkyl such as methyl, ethyl, n- or i-propyl or n-, i- or t-butyl or $C_2$- to $C_4$-alkenyl such as ethenyl, 1-propenyl, 2-propenyl, 1-butenyl, 2-butenyl or 3-butenyl, hydroxyl and halogen such as F, Cl, and Br. If appropriate, the abovementioned alkyl or alkenyl substituents may also have a keto or aldehyde group; examples are propan-2-on-3-yl, butan-2-on-4-yl, 3-buten-2-on-4-yl. Nonlimiting examples of suitable heterocyclic substrates are, in particular, binuclear heterocycles such as indole, N-methylindole and the analogs thereof which are substituted on carbon atoms by one to three substituents, such as, for example, 5-chloroindole or 5-bromoindole, and also quinoline and quinoline derivatives such as, for example, 8-methylquinoline, 6-methylquinoline and quinaldin; and benzothiophene and the analogs thereof which are substituted on carbon atoms by one to three substituents. Others which may be mentioned are trinuclear heteroaromatics such as acridine, and the analogs thereof which are substituted on carbon atoms by one to three substituents.

Substrates of group b) which can be oxidized in accordance with the invention are optionally substituted mono- or polynuclear, in particular mono- or binuclear, aromatics such as benzene and naphthaline. If appropriate, the aromatic compounds can be mono- or polysubstituted and have for example 1 to 5 substituents attached to the ring carbon atoms. Examples of suitable substituents are $C_1$- to $C_4$-alkyl such as methyl, ethyl, n- or i-propyl or n-, i- or t-butyl, or $C_2$- to $C_4$-alkenyl such as ethenyl, 1-propenyl, 2-propenyl, 1-butenyl, 2-butenyl or 3-butenyl, hydroxyl and halogen such as F, Cl, and Br. If appropriate, the abovementioned alkyl or alkenyl substituents may also have a keto or aldehyde group; examples are propan-2-on-3-yl, butan-2-on-4-yl, 3-buten-2-on-4-yl. If appropriate, the aromatic ring can be fused to a four- to seven-membered nonaromatic ring. If appropriate, the nonaromatic ring can have one or two C-C double bonds, be mono- or polysubstituted by abovementioned substituents and, if appropriate, have attached to it one or two ring hetero atoms. Examples of particularly useful aromatics are mononuclear aromatics such as cumene, and binuclear substrates such as indene and naphthalene, and the analogs thereof which are substituted on carbon atoms by one to three substituents.

Substrates of group c) which can be oxidized in accordance with the invention are straight-chain or branched alkanes or alkenes having 4 to 15, preferably 6 to 12, carbon atoms. Examples which may be mentioned are n-pentane, n-hexane, n-heptane, n-octane, n-nonane, n-decane, n-undecane and n-dodecane, and the analogs of these compounds which have one or more branchings such as, for example, analogous compounds with 1 to 3 methyl side groups; or the mono- or polyunsaturated, preferably monounsaturated, analogs of the abovementioned alkanes.

Substrates of group d) which can be oxidized in accordance with the invention are optionally substituted cycloalkanes and cycloalkenes. Examples are cyclopentane, cyclopentene, cyclohexane, cyclohexene, cycloheptane and cycloheptene. In this context, the ring structure can be mono- or polysubstituted and can have attached to it for example 1 to 5 substituents as defined above for compounds of groups a) and b). A nonlimiting example are ionones, such as $\alpha$-, $\beta$- and $\gamma$-ionone, and the corresponding methylionones and isomethylionones.

Substrates of group e) which can be oxidized in accordance with the invention are straight-chain or branched, saturated or mono- or polyunsaturated $C_8$-$C_{30}$-carboxylic acids, in particular monocarboxylic acids, or carboxylic acid derivatives thereof, such as esters and amides. Examples which can be mentioned are saturated monocarboxylic acids which can be hydroxylated terminally or subterminally ($\omega$-1-, $\omega$-2- or $\omega$-3 position).

Subject matter of the invention are also nucleic acid sequences (single- and double-stranded DNA and RNA sequences) encoding one of the above monooxygenases, and their functional equivalents. Further nucleic acid sequences according to the invention are derived from SEQ ID NO:1 and differ therefrom by addition, substitution, insertion or deletion of single or more than one nucleotides, with the continued encoding of monooxygenase with the desired spectrum of properties.

Also encompassed in accordance with the invention are those nucleic acid sequences which encompass what is known as silent mutations or which are altered in accordance with the codon usage of a specific organism of origin, or a host organism, in comparison with a specifically mentioned sequence, as are naturally occurring variants such as, for example, splice variants, thereof. Subject matter are also sequences which can be obtained by conservative nucleotide substitutions (i.e. the amino acid in question is replaced by an amino acid of the same charge, size, polarity and/or solubility).

The invention furthermore encompasses nucleic acid sequences which hybridize with abovementioned coding sequences or are complementary thereto. These polynucleotides can be found by screening genomic libraries or cDNA libraries and, if appropriate, amplified therefrom using suitable primers by means of PCR and subsequently isolated, for example using suitable probes. Another possibility is the transformation of suitable microorganisms with polynucleotides or vectors according to the invention, the multiplication of the microorganisms and thus the amplification of the polynucleotides, and their subsequent isolation. Moreover, polynucleotides according to the invention can also be synthesized chemically.

The property of being able to "hybridize" with polynucleotides is understood as the ability of a polynucleotide or oligonucleotide to bind to a virtually complementary sequence under stringent conditions, while unspecific binding events between noncomplementary partners do not take place under these conditions. Here, the sequences should have 70-100%, preferably 90-100%, complementarity. The property of complementary sequences of being able specifically to bind to each other is exploited for example in the Northern or Southern blot technique, or for binding primers in PCR or RT-PCR. Oligonucleotides starting from a length of 30 base pairs are normally employed for this purpose. Stringent conditions are understood as meaning, for example for the Northern blot technique, the use of a wash solution at a temperature of 50-70° C., preferably 60-65° C., for example 0.1×SSC buffer with 0.1% SDS (20×SSC: 3M NaCl, 0.3M sodium citrate, pH 7.0) for eluting unspecifically hybridized cDNA probes or oligonucleotides. As has been mentioned above, only nucleic acids with a high degree of complementarity remain bound to each other in this process.

Subject matter of the invention are furthermore expression constructs containing, under the genetic control of regulatory nucleic acid sequences, a nucleic acid sequence encoding a mutant according to the invention; and vectors encompassing at least one of these expression constructs. Such constructs according to the invention preferably encompass a promoter 5'-upstream and a terminator sequence 3'-downstream of the coding sequence in question, and, if appropriate, further customary regulatory elements, in each case linked operably to the coding sequence. "Operable linkage" is understood as meaning the sequential arrangement of promoter, coding sequence, terminator and, if appropriate, further regulatory elements in such a way that each of the regulatory elements can fulfill its function as intended upon the expression of the coding sequence. Examples of sequences which can be linked operably are targeting sequences, and also translation and other enhancers, polyadenylation signals and the like. Further regulatory elements encompass selectable markers, amplification signals, replication origins and the like.

The natural regulatory sequence may still be present before the actual structural gene, in addition to the artificial regulatory sequences. If appropriate, genetic modification can be used to switch off this natural regulation and to increase or reduce the expression of the genes. However, the gene construct may also have a simpler structure, that is to say no additional regulatory signals are inserted before the structural gene and the natural promoter together with its regulation is not removed. Instead, the natural regulatory sequence is mutated in such a way that regulation no longer takes place and gene expression is increased or reduced. One or more copies of the nucleic acid sequences may be present in the gene construct.

Examples of useful promoters are: cos, tac, trp, tet, trp-tet, lpp, lac, lpp-lac, lacIq, T7, T5, T3, gal, trc, ara, SP6, l-PR or the l-PL promoter, all of which are advantageously used in Gram-negative bacteria; and the Gram-positive promoters amy and SPO2, the yeast promoters ADC1, MFa, AC, P-60, CYC1, GAPDH or the plant promoters CaMV/35S, SSU, OCS, lib4, usp, STLS1, B33, not, or the ubiquitin or phaseolin promoter. The use of inducible promoters, such as, for example, light-inducible and, in particular, temperature-inducible promoters, such as the $P_rP_l$, promoter, is especially preferred.

In principle, all natural promoters together with their regulatory sequences can be used. In addition, synthetic promoters can also be used advantageously.

The abovementioned regulatory sequences are intended to make possible the targeted expression of the nucleic acid sequences and protein expression. Depending on the host organism, this may mean, for example, that the gene is expressed or overexpressed only after induction, or that it is expressed and/or overexpressed immediately.

The regulatory sequences or factors can preferably have a positive effect on expression and thus increase or reduce it. Thus, the regulatory elements can be enhanced advantageously at the transcriptional level by using strong transcription signals such as promoters and/or enhancers. In addition, enhanced translation is also possible, for example by improving mRNA stability.

An expression cassette is prepared by fusing a suitable promoter to a suitable monooxygenase nucleotide sequence and to a terminator or polyadenylation signal. Customary recombination and clone techniques are used for this purpose as they are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found, for example, in "Cloning Vectors" (Pouwels P. H. et al., Ed., Elsevier, Amsterdam-New York-Oxford, 1985). In addition to plasmids, vectors are also understood as meaning all of the other vectors known to the skilled worker, such as, for example, phages, viruses such as SV40, CMV, baculovirus and adenovirus, transposons, IS elements, phasmids, cosmids and linear or circular DNA. These vectors can be replicated autonomously in the host organism or replicated chromosomally.

Recombinant microorganisms which, for example, are transformed with at least one vector according to the invention and which can be employed for producing the mutants can be generated with the aid of the vectors according to the invention. Advantageously, the above-described recombinant constructs according to the invention are introduced into, and expressed in, a suitable host system. To do so, cloning and transfection processes which the skilled worker is familiar with, such as, for example, coprecipitation, protoplast fusion, electroporation, retroviral transfection and the like are preferably used in order to express the nucleic acids mentioned in the expression system in question. Suitable systems are described, for example, in Current Protocols in Molecular Biology, F. Ausubel et al., Ed., Wiley Interscience, New York 1997.

Suitable as host organisms are, in principle, all the organisms which make possible an expression of the nucleic acids according to the invention, their allelic variants, their functional equivalents or derivatives. Host organisms are understood as meaning, for example, bacteria, fungi, yeasts, plant or animal cells. Preferred organisms are bacteria such as those of the genera *Escherichia*, such as, for example, *Escherichia coli, Streptomyces, Bacillus* or *Pseudomonas*, eukaryotic microorganisms such as *Saccharomyces cerevisiae, Aspergillus*, higher eukaryotic cells from animals or plants, for example Sf9 or CHO cells.

Successfully transformed organisms can be selected by means of marker genes which are also present in the vector or in the expression cassette. Examples of such marker genes are genes for resistance to antibiotics and for enzymes which catalyze a coloring reaction which causes staining of the transformed cell. The latter can then be selected by means of automatic cell sorting. Microorganisms which are transformed successfully with a vector and which carry a relevant gene for resistance to antibiotics (for example G418 or hygromycin) can be selected by suitable liquid or solid media comprising antibiotics. Marker proteins which are presented on the cell surface can be utilized for selection by means of affinity chromatography.

The combination of the host organisms and the vectors which match the organisms, such as plasmids, viruses or phages, such as, for example, plasmids with the RNA polymerase/promoter system, phages λ or μ or other temperent phages or transposons and/or further advantageous regulatory sequences forms an expression system. For example, the term "expression system" refers to the combination of mammalian cells such as CHO cells, and vectors such as pcDNA3neo vector, which are suitable for mammalian cells.

If desired, the gene product can also be expressed in transgenic organisms such as transgenic animals, such as, in particular, mice or sheep, or transgenic plants.

Subject-matter of the invention are furthermore processes for the recombinant production of a monooxygenase according to the invention, wherein a monooxygenase-producing microorganism is grown, and the expression of monooxygenase is, if appropriate, induced, and the monooxygenase is isolated from the culture. Thus, the monooxygenase can also be produced on an industrial scale if so desired.

The recombinant microorganism can be grown and fermented by known processes. For example, bacteria can be multiplied in TB or LB medium and at a temperature of from 20 to 40° C. and a pH of from 6 to 9. Specific suitable culture conditions are described, for example, in T. Maniatis, E. F. Fritsch and J. Sambrook, Molecular Cloning: A Laboratory Manual, Cold Spring Harbor Laboratory, Cold Spring Harbor, N.Y. (1989).

Unless the monooxygenase is secreted into the culture medium, the cells are then disrupted and the enzyme is obtained from the lysate by known protein isolation processes. The cells can be disrupted by a process of choice selected from among high-frequency ultrasound, high pressure such as, for example, in a French press, osmolysis, the action of detergents, lytic enzymes or organic solvents, homogenizers or a combination of more than one of the processes stated.

Purification of the monooxygenase can be achieved by known chromatographic processes such as chromatography with molecular sieve (gel filtration) such as Q-Sepharose chromatography, ion exchange chromatography and hydrophobic chromatography, and with other customary processes such as ultrafiltration, crystallization, salting out, dialysis and native gel electrophoresis. Suitable processes are described, for example, in Cooper, F. G., Biochemische Arbeitsprocessen [processes in Biochemistry], Verlag Walter de Gruyter, Berlin, New York or in Scopes, R., Protein Purification, Springer Verlag, New York, Heidelberg, Berlin.

To isolate the recombinant protein, it is particularly advantageous to use vector systems or oligonucleotides which extend the cDNA by specific nucleotide sequences and thus encode modified polypeptide or fusion proteins in order to simplify purification. Such suitable modifications are, for example, what is known as "tags" which have an anchoring function, such as, for example, the modification known as hexa-histidine anchor, or epitopes which can be recognized by antibodies as antigens (described, for example, in Harlow, E. and Lane, D., 1988, Antibodies: A Laboratory Manual. Cold Spring Harbor (N.Y.) Press). These anchors can serve for attaching the proteins to a solid support, such as, for example, a polymer matrix, with which for example a chromatographic column can be packed, or they can be used on a microtiter plate or any other support.

These anchors can simultaneously also be used for recognizing the proteins. Others which can be used for recognizing the proteins are furthermore customary labels such as fluorescent dyes, enzyme labels which, after reaction with a substrate, form a detectable reaction product, or radiolabels, alone or in combination with the anchors for derivatizing the proteins.

The invention furthermore relates to a process for the microbiological oxidation of organic compounds of the above type.

If the conversion is carried out with the recombinant microorganism, the microorganisms are preferably first grown in the presence of oxygen and in a complex medium such as, for example, TB or LB medium, at a culture temperature of approximately 20° C. or more and a pH of approximately 6 to 9 until a sufficient cell density is reached. In order to better govern the oxidation reaction, the use of an inducible promoter is preferred. After induction of the monooxygenase production, culturing is continued for 12 hours to 3 days in the presence of oxygen.

If, in contrast, the conversion in accordance with the invention is carried out with purified or concentrated enzyme, the enzyme according to the invention is dissolved in a medium comprising an exogenous substrate (approx. 0.01 to 10 mM or 0.05 to 5 mM) and the conversion is carried out at a temperature of approximately 10° C. or more and a pH of approximately 6 to 9 (such as, for example, adjusted with 100 to 200 mM phosphate buffer or Tris buffer), preferably in the presence of oxygen, and in the presence of a reducing agent, the substrate-comprising medium additionally comprising an approximately 10- to 100-fold molar excess of reduction equivalents based on the substrate to be oxidized. Preferred reducing agent is NADPH.

In the substrate oxidation process according to the invention, oxygen which is present in the reaction medium or has been added is subjected to enzymatic reductive cleavage. The reduction equivalents required are provided by the reducing agent added (electron donor).

The oxidation product formed can then be separated from the medium and purified in the customary fashion such as, for example, by extraction or chromatography.

The following nonlimiting examples describe specific embodiments of the invention.

General Experimental Data a) General Cloning Processes

The cloning steps carried out within the present invention such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, phage multiplication and sequence analysis of recombinant DNA were carried out as described by Sambrook et al. (1989) loc. cit.

b) Polymerase Chain Reaction (PCR)

PCR was carried out by standard protocol with the following standard reaction mix:

8 μl of dNTP mix (200 μM), 10 μl of Taq polymerase buffer (10×) without $MgCl_2$, 8 μl $MgCl_2$ (25 μM), in each case 1 μl of primer (0.1 μM), 1 μl of DNA to be amplified, 2.5 U of Taq polymerase (MBI Fermentas, Vilnius, Lithuania), demineralized water to 100 μl.

c) Culturing *E. coli*

Recombinant *E. coli* strains DH5α were cultured in LB-Amp medium (Tryptone 10.0 g, NaCl 5.0 g, yeast extract 5.0 g, Ampicillin 100 g/ml H₂O to 1000 ml) at 37° C. To this end, in each case one colony was transferred from an agar plate to 5 ml LB-Amp by means of a loop. After culturing for approx. 18 hours at a shake frequency of 220 rpm, 400 ml of medium in a 2 l flask were inoculated with 4 ml of culture. The P450 expression in *E. coli* was induced after an OD578 value of between 0.8 and 1.0 had been reached by heat-shock induction at 42° C. for three to four hours.

d) Cell Disruption

Cell pellets with a biomass fresh weight of up to 15 g of *E. coli* DH5α were defrosted on ice and suspended in 25 ml of potassium phosphate buffer (50 mM, pH 7.5, 1 mM EDTA) or Tris/HCl buffer (50 mM, pH 7.5, 1 mM EDTA). The *E. coli* cell suspension, which was cooled on ice, was disrupted by means of sonication for 3 minutes (Branson Sonifier W250, (Dietzenbach, Germany), power output 80 W, operating interval 20%). Prior to protein purification, the cell suspension was centrifuged for 20 minutes at 32.500 g and filtered through a 0.22 mm Sterivex-GP filter (Millipore), yielding a crude extract.

EXAMPLE 1

Cloning and Expression of P450 from *Thermus thermophilus* HB27 and its his-tag Derivatives 1. Cloning of P450 from *Thermus thermophilus* HB27

The coding P450 sequence (blunt ended) was cloned into the HincII cleavage site of plasmid pTZ19R (MBI Fermentas). The coding P450 sequence was amplified from the resulting plasmid TTHB66 with the aid of PCR. The following primers were used for this purpose:
a) 30-mer sense oligonucleotide comprising the NdeI cleavage site (italicized) as part of the P450 ATG start codon:
5'-CGAAGCTC*ATATG*AAGCGCCTTTCCCTGAG (SEQ ID NO:7).
b) 30-mer antisense oligonucleotide comprising the EcoRI cleavage site (italicized) as part of the TGA stop codon:
5'-GC*GAATTC*ACGCCCGCACCTCCTCCCTAGG (SEQ ID NO:8).

The resulting fragment was cloned into the NdeI cleavage sites of vector pCYTEXP1 (plasmid with the temperature-inducible P$_R$P$_L$ promoter system of bacteriophage λ (Belev T. N., et al., Plasmid (1991) 26:147)) and transformed into *E. coli* DH-5α (Clontech, Heidelberg).

*E. coli* DH-5α, comprising the plasmid of interest, was inoculated into LB medium in the presence of Ampicillin and the culture was incubated-overnight at 37° C. Some of the sample was inoculated into fresh LB medium (in the presence of Ampicillin), and the resulting culture was grown at 37° C. to OD=0.9. Induction was affected by raising the temperature to 42° C. over a period of 24 hours. The change in the P450 content during expression was determined by measuring the CO difference spectrum.

| Expression time [h] | ΔA$_{450-490}$ | P450 concentration [μM] |
|---|---|---|
| 4 | 0.092 | 0.056 |
| 8 | 0.176 | 0.106 |
| 24 | 0.106 | 0.064 |

2. Cloning P450 from *Thermus thermophilus* HB27 with N-terminal his tag

The coding P450 sequence was amplified from plasmid TTHB66 by PCR using the following primers:
(a) 50-mer sense oligonucleotide comprising the NdeI cleavage site (italicized) as part of the P450 ATG start codon and the tag-coding codons (underlined):
5'-CGAAGCTC*ATATG*<u>CATCACCATCATC</u>ATCACAAGCGCCTTTC (SEQ ID NO:9);
(b) 30-mer antisense oligonucleotide comprising the EcoRI cleavage site (italicized) as part of the TGA stop codon:
5'-GC*GAATTC*ACGCCCGCACCTCCTCCCTAGG (SEQ ID NO:8).

The resulting fragment was cloned into the NdeI and EcoRI cleavage sites of vector p-CYTEXP1 and expressed in *E. coli* DH-5α.

*E. coli* DH-5α, comprising the plasmid of interest, was inoculated into LB medium in the presence of Ampicillin and the culture was incubated overnight at 37° C. Some of the sample was inoculated into fresh LB medium (in the presence of Ampicillin), and the resulting culture was grown at 37° C. to OD=0.9. Induction was affected by raising the temperature to 42° C. over a period of 24 hours. The change in the P450 content during expression was determined by measuring the CO difference spectrum.

| Expression time [h] | ΔA$_{450-490}$ | P450 concentration [μM] |
|---|---|---|
| 4 | ND | ND |
| 8 | 0.097 | 0.073 |
| 24 | 0.111 | 0.073 |

3. Cloning P450 from *Thermus thermophilus* HB27 with C-terminal his tag

The coding P450 sequence was amplified from plasmid TTHB66 by PCR using the following primers:
(a) 30-mer sense oligonucleotide comprising the NdeI cleavage site (italicized) as part of the P450 ATG start codon:
5'-CGAAGCTC*ATATG*AAGCGCCTTTCCCTGAG (SEQ ID NO:7)
(b) 47-mer antisense oligonucleotide comprising the EcoRI cleavage site (italicized) as part of the TGA stop codon and the underlined tag-encoding part sequence:
5'-CG*GAATTC*A<u>GTGATGATGATGGTGATG</u>CGCCCGCACCTCCTC (SEQ ID NO:10).

The resulting fragment was cloned into the NdeI and EcoRI cleavage sites of vector p-CYTEXP1 and expressed in *E. coli* DH-5α.

*E. coli* DH-5α, comprising the plasmid of interest, was inoculated into LB medium in the presence of Ampicillin and the culture was incubated overnight at 37° C. Some of the sample was inoculated into fresh LB medium (in the presence of Ampicillin), and the resulting culture was grown at 37° C. to OD=0.9. Induction was affected by raising the temperature to 42° C. over a period of 24 hours. The change in the P450 content during expression was determined by measuring the CO difference spectrum.

| Expression time [h] | ΔA$_{450-490}$ | P450 concentration [μM] |
|---|---|---|
| 4 | ND | ND |
| 8 | 0.1 | 0.075 |
| 24 | ND | ND |

EXAMPLE 2

Determination of the Thermostability of *Thermus thermophilus* P450 in Comparison with P450 BM3

The two enzymes were incubated in each case for 30 minutes in Tris/HCl buffer pH 7.5, 25 mM, at different temperatures. The reaction mixtures were subsequently cooled and the P450 concentration was determined spectrometrically. The results are compiled in the table which follows and shown in FIG. 2 in the form of a graph.

| Temperature [° C.] | | 30 | 40 | 50 | 60 |
|---|---|---|---|---|---|
| P450 concentration [%] | P450 thermus | 100 | 89 | 29 | 22 |
| | P450 BM3 | 92 | 63 | 0 | 0 |

As can be seen from the test results, the enzyme according to the invention has a significantly higher thermostability after incubation for 30 minutes at all temperatures.

EXAMPLE 3

Biotransformation Experiments

It has hitherto not been possible unambiguously to identify the endogenous redox partner for the *T. thermophilus* cytochrome P450 [lacuna] according to the invention. However, enzyme activity was observed, for example, during the hydroxylation of β- and/or α-ionone. With β-ionone as substrate, conversion into a main product was observed, whereupon α-ionone was converted into a product mixture. A comparison with synthetic standards revealed that the main product of the conversion of β-ionone is 4-hydroxy-β-ionone.

Precultures of *T. thermophilus* [5 ml of Tt medium (2 g of yeast extract, 1 g of tryptone, 1 g of NaCl in 500 ml of deionized water)] were inoculated from agar plate cultures and incubated for 24 hours at 65° C. with shaking (150 rpm). Subsequently 100 ml of the Tt medium were inoculated with the preculture and incubated at 65° C. with shaking.

β-Ionone (107 μl/ml of culture) was added to each culture after 24 hours. Cultivation was continued for 78 hours. The cells were removed by centrifugation and the supernatant was extracted with diethyl ether. The extract was analyzed by GC and TLC. Control cultures without substrate were prepared and analyzed under identical conditions.

---

We claim:

1. An isolated cytochrome P450 monooxygenase having the amino acid sequence of
    SEQ ID NO: 2 or;
    an amino acid sequence having at least 95% homology with SEQ ID NO: 2.

2. The isolated cytochrome P450 monooxygenase as claimed in claim 1 which is from bacteria of the genus *Thermus* sp.

3. The isolated cytochrome P450 monooxygenase as claimed in claim 2 which is from a bacterium of the species *Thermus thermophilus*.

4. A process for the microbiological oxidation of an organic compound, wherein this compound is converted with at least one isolated cytochrome P450 monooxygenase as claimed in claim 1 and wherein the compound is selected from among:
    optionally substituted N-, O- or S-heterocyclic mono-, bi- or polynuclear aromatic compounds;
    optionally substituted mono- or polynuclear aromatics;
    straight-chain or branched alkanes and alkenes;
    optionally substituted cycloalkanes and cycloalkenes; and
    aliphatic (terminally saturated) carboxylic acids.

5. A bioreactor encompassing the isolated cytochrome P450 monooxygenase as claimed in claim 1.

* * * * *

SEQUENCE LISTING

<160> NUMBER OF SEQ ID NOS: 11

<210> SEQ ID NO 1
<211> LENGTH: 1170
<212> TYPE: DNA
<213> ORGANISM: Thermus thermophilus
<220> FEATURE:
<221> NAME/KEY: CDS
<222> LOCATION: (1)..(1170)

<400> SEQUENCE: 1

```
atg aag cgc ctt tcc ctg agg gag gcc tgg ccc tac ctg aaa gac ctc      48
Met Lys Arg Leu Ser Leu Arg Glu Ala Trp Pro Tyr Leu Lys Asp Leu
 1               5                  10                  15 cag caa gat ccc ctc gcc gtc ctg ctg gcg tgg ggc cgg gcc cac ccc      96
Gln Gln Asp Pro Leu Ala Val Leu Leu Ala Trp Gly Arg Ala His Pro
             20                  25                  30 cgg ctc ttc ctt ccc ctg ccc cgc ttc ccc ctg gcc ctg atc ttt gac     144
Arg Leu Phe Leu Pro Leu Pro Arg Phe Pro Leu Ala Leu Ile Phe Asp
         35                  40                  45 ccc gag ggg gtg gag ggg gcg ctc ctc gcc gag ggg acc acc aag gcc     192
Pro Glu Gly Val Glu Gly Ala Leu Leu Ala Glu Gly Thr Thr Lys Ala
     50                  55                  60 acc ttc cag tac cgg gcc ctc tcc cgc ctc acg ggg agg ggc ctc ctc     240
Thr Phe Gln Tyr Arg Ala Leu Ser Arg Leu Thr Gly Arg Gly Leu Leu
 65                  70                  75                  80 acc gac tgg ggg gaa agc tgg aag gag gcg cgc aag gcc ctc aaa gac     288
Thr Asp Trp Gly Glu Ser Trp Lys Glu Ala Arg Lys Ala Leu Lys Asp
                 85                  90                  95 ccc ttc ctg ccg aag aac gtc cgc ggc tac cgg gag gcc atg gag gag     336
Pro Phe Leu Pro Lys Asn Val Arg Gly Tyr Arg Glu Ala Met Glu Glu
```

```
gag gcc cgg gcc ttc ttc ggg gag tgg cgg ggg gag gag cgg gac ctg      384
Glu Ala Arg Ala Phe Phe Gly Glu Trp Arg Gly Glu Glu Arg Asp Leu
            115                 120                 125 gac cac gag atg ctc gcc ctc tcc ctg cgc ctc ctc ggg cgg gcc ctc      432
Asp His Glu Met Leu Ala Leu Ser Leu Arg Leu Leu Gly Arg Ala Leu
    130                 135                 140 ttc ggg aag ccc ctc tcc cca agc ctc gcg gag cac gcc ctt aag gcc      480
Phe Gly Lys Pro Leu Ser Pro Ser Leu Ala Glu His Ala Leu Lys Ala
145                 150                 155                 160 ctg gac cgg atc atg gcc cag acc agg agc ccc ctg gcc ctc ctg gac      528
Leu Asp Arg Ile Met Ala Gln Thr Arg Ser Pro Leu Ala Leu Leu Asp
                165                 170                 175 ctg gcc gcc gaa gcc cgc ttc cgg aag gac cgg ggg gcc ctc tac cgc      576
Leu Ala Ala Glu Ala Arg Phe Arg Lys Asp Arg Gly Ala Leu Tyr Arg
            180                 185                 190 gag gcg gaa gcc ctc atc gtc cac ccg ccc ctc tcc cac ctt ccc cga      624
Glu Ala Glu Ala Leu Ile Val His Pro Pro Leu Ser His Leu Pro Arg
        195                 200                 205 gag cgc gcc ctg agc gag gcc gtg acc ctc ctg gtg gcg ggc cac gag      672
Glu Arg Ala Leu Ser Glu Ala Val Thr Leu Leu Val Ala Gly His Glu
    210                 215                 220 acg gtg gcg agc gcc ctc acc tgg tcc ttt ctc ctc ctc tcc cac cgc      720
Thr Val Ala Ser Ala Leu Thr Trp Ser Phe Leu Leu Leu Ser His Arg
225                 230                 235                 240 ccg gac tgg cag aag cgg gtg gcc gag agc gag gag gcg gcc ctc gcc      768
Pro Asp Trp Gln Lys Arg Val Ala Glu Ser Glu Glu Ala Ala Leu Ala
                245                 250                 255 gcc ttc cag gag gcc ctg agg ctc tac ccc ccc gcc tgg atc ctc acc      816
Ala Phe Gln Glu Ala Leu Arg Leu Tyr Pro Pro Ala Trp Ile Leu Thr
            260                 265                 270 cgg agg ctg gaa agg ccc ctc ctc ctg gga gag gac cgg ctc ccc ccg      864
Arg Arg Leu Glu Arg Pro Leu Leu Leu Gly Glu Asp Arg Leu Pro Pro
        275                 280                 285 ggc acc acc ctg gtc ctc tcc ccc tac gtg acc cag agg ctc cac ttc      912
Gly Thr Thr Leu Val Leu Ser Pro Tyr Val Thr Gln Arg Leu His Phe
    290                 295                 300 ccc gat ggg gag gcc ttc cgg ccc gag cgc ttc ctg gag gaa agg ggg      960
Pro Asp Gly Glu Ala Phe Arg Pro Glu Arg Phe Leu Glu Glu Arg Gly
305                 310                 315                 320 acc cct tcg ggg cgc tac ttc ccc ttt ggc ctg ggg cag agg ctc tgc     1008
Thr Pro Ser Gly Arg Tyr Phe Pro Phe Gly Leu Gly Gln Arg Leu Cys
                325                 330                 335 ctg ggg cgg gac ttc gcc ctc ctc gag ggc ccc atc gtc ctc agg gcc     1056
Leu Gly Arg Asp Phe Ala Leu Leu Glu Gly Pro Ile Val Leu Arg Ala
            340                 345                 350 ttc ttc cgc cgc ttc cgc cta gac ccc ctc ccc ttc ccc cgg gtc ctc     1104
Phe Phe Arg Arg Phe Arg Leu Asp Pro Leu Pro Phe Pro Arg Val Leu
        355                 360                 365 gcc cag gtc acc ctg agg ccc gaa ggc ggg ctt ccc gcg cgg cct agg     1152
Ala Gln Val Thr Leu Arg Pro Glu Gly Gly Leu Pro Ala Arg Pro Arg
    370                 375                 380 gag gag gtg cgg gcg tga                                              1170
Glu Glu Val Arg Ala
385
```

<210> SEQ ID NO 2
<211> LENGTH: 389
<212> TYPE: PRT
<213> ORGANISM: Thermus thermophilus

<400> SEQUENCE: 2

```
Met Lys Arg Leu Ser Leu Arg Glu Ala Trp Pro Tyr Leu Lys Asp Leu
 1               5                  10                  15
Gln Gln Asp Pro Leu Ala Val Leu Leu Ala Trp Gly Arg Ala His Pro
            20                  25                  30
Arg Leu Phe Leu Pro Leu Pro Arg Phe Pro Leu Ala Leu Ile Phe Asp
        35                  40                  45
Pro Glu Gly Val Glu Gly Ala Leu Leu Ala Glu Gly Thr Thr Lys Ala
    50                  55                  60
Thr Phe Gln Tyr Arg Ala Leu Ser Arg Leu Thr Gly Arg Gly Leu Leu
65                  70                  75                  80
Thr Asp Trp Gly Glu Ser Trp Lys Glu Ala Arg Lys Ala Leu Lys Asp
            85                  90                  95
Pro Phe Leu Pro Lys Asn Val Arg Gly Tyr Arg Glu Ala Met Glu Glu
        100                 105                 110
Glu Ala Arg Ala Phe Phe Gly Glu Trp Arg Gly Glu Arg Asp Leu
    115                 120                 125
Asp His Glu Met Leu Ala Leu Ser Leu Arg Leu Leu Gly Arg Ala Leu
        130                 135                 140
Phe Gly Lys Pro Leu Ser Pro Ser Leu Ala Glu His Ala Leu Lys Ala
145                 150                 155                 160
Leu Asp Arg Ile Met Ala Gln Thr Arg Ser Pro Leu Ala Leu Leu Asp
                165                 170                 175
Leu Ala Ala Glu Ala Arg Phe Arg Lys Asp Arg Gly Ala Leu Tyr Arg
            180                 185                 190
Glu Ala Glu Ala Leu Ile Val His Pro Pro Leu Ser His Leu Pro Arg
        195                 200                 205
Glu Arg Ala Leu Ser Glu Ala Val Thr Leu Leu Val Ala Gly His Glu
    210                 215                 220
Thr Val Ala Ser Ala Leu Thr Trp Ser Phe Leu Leu Leu Ser His Arg
225                 230                 235                 240
Pro Asp Trp Gln Lys Arg Val Ala Glu Ser Glu Ala Ala Leu Ala
                245                 250                 255
Ala Phe Gln Glu Ala Leu Arg Leu Tyr Pro Pro Ala Trp Ile Leu Thr
            260                 265                 270
Arg Arg Leu Glu Arg Pro Leu Leu Gly Glu Asp Arg Leu Pro Pro
        275                 280                 285
Gly Thr Thr Leu Val Leu Ser Pro Tyr Val Thr Gln Arg Leu His Phe
    290                 295                 300
Pro Asp Gly Glu Ala Phe Arg Pro Glu Arg Phe Leu Glu Glu Arg Gly
305                 310                 315                 320
Thr Pro Ser Gly Arg Tyr Phe Pro Phe Gly Leu Gly Gln Arg Leu Cys
                325                 330                 335
Leu Gly Arg Asp Phe Ala Leu Leu Glu Gly Pro Ile Val Leu Arg Ala
            340                 345                 350
Phe Phe Arg Arg Phe Arg Leu Asp Pro Leu Pro Phe Pro Arg Val Leu
        355                 360                 365
Ala Gln Val Thr Leu Arg Pro Glu Gly Gly Leu Pro Ala Arg Pro Arg
    370                 375                 380
Glu Glu Val Arg Ala
385
```

```
<210> SEQ ID NO 3
<211> LENGTH: 1188
<212> TYPE: DNA
<213> ORGANISM: Artificial sequence
<220> FEATURE:
<221> NAME/KEY: misc_feature
<222> LOCATION: (4)..(21)
<223> OTHER INFORMATION: His tag
<220> FEATURE:
<223> OTHER INFORMATION: Description of artificial sequence:N-terminal
      his tagged
<220> FEATURE:
<221> NAME/KEY: CDS
<222> LOCATION: (1)..(1188)

<400> SEQUENCE: 3
```

| | | | | | | | | | | | | | | | | |
|---|---|---|---|---|---|---|---|---|---|---|---|---|---|---|---|---|
| atg | cat | cac | cat | cat | cat | cac | aag | cgc | ctt | tcc | ctg | agg | gag | gcc | tgg | 48 |
| Met | His | His | His | His | His | His | Lys | Arg | Leu | Ser | Leu | Arg | Glu | Ala | Trp | |
| 1 | | | | 5 | | | | | 10 | | | | | 15 | | |
| ccc | tac | ctg | aaa | gac | ctc | cag | caa | gat | ccc | ctc | gcc | gtc | ctg | ctg | gcg | 96 |
| Pro | Tyr | Leu | Lys | Asp | Leu | Gln | Gln | Asp | Pro | Leu | Ala | Val | Leu | Leu | Ala | |
| | | | 20 | | | | | 25 | | | | | 30 | | | |
| tgg | ggc | cgg | gcc | cac | ccc | cgg | ctc | ttc | ctt | ccc | ctg | ccc | cgc | ttc | ccc | 144 |
| Trp | Gly | Arg | Ala | His | Pro | Arg | Leu | Phe | Leu | Pro | Leu | Pro | Arg | Phe | Pro | |
| | | 35 | | | | | 40 | | | | | 45 | | | | |
| ctg | gcc | ctg | atc | ttt | gac | ccc | gag | ggg | gtg | gag | ggg | gcg | ctc | ctc | gcc | 192 |
| Leu | Ala | Leu | Ile | Phe | Asp | Pro | Glu | Gly | Val | Glu | Gly | Ala | Leu | Leu | Ala | |
| 50 | | | | | 55 | | | | | 60 | | | | | | |
| gag | ggg | acc | acc | aag | gcc | acc | ttc | cag | tac | cgg | gcc | ctc | tcc | cgc | ctc | 240 |
| Glu | Gly | Thr | Thr | Lys | Ala | Thr | Phe | Gln | Tyr | Arg | Ala | Leu | Ser | Arg | Leu | |
| 65 | | | | | 70 | | | | | 75 | | | | | 80 | |
| acg | ggg | agg | ggc | ctc | ctc | acc | gac | tgg | ggg | gaa | agc | tgg | aag | gag | gcg | 288 |
| Thr | Gly | Arg | Gly | Leu | Leu | Thr | Asp | Trp | Gly | Glu | Ser | Trp | Lys | Glu | Ala | |
| | | | | 85 | | | | | 90 | | | | | 95 | | |
| cgc | aag | gcc | ctc | aaa | gac | ccc | ttc | ctg | ccg | aag | aac | gtc | cgc | ggc | tac | 336 |
| Arg | Lys | Ala | Leu | Lys | Asp | Pro | Phe | Leu | Pro | Lys | Asn | Val | Arg | Gly | Tyr | |
| | | | 100 | | | | | 105 | | | | | 110 | | | |
| cgg | gag | gcc | atg | gag | gag | gag | gcc | cgg | gcc | ttc | ttc | ggg | gag | tgg | cgg | 384 |
| Arg | Glu | Ala | Met | Glu | Glu | Glu | Ala | Arg | Ala | Phe | Phe | Gly | Glu | Trp | Arg | |
| | | 115 | | | | | 120 | | | | | 125 | | | | |
| ggg | gag | gag | cgg | gac | ctg | gac | cac | gag | atg | ctc | gcc | ctc | tcc | ctg | cgc | 432 |
| Gly | Glu | Glu | Arg | Asp | Leu | Asp | His | Glu | Met | Leu | Ala | Leu | Ser | Leu | Arg | |
| 130 | | | | | 135 | | | | | 140 | | | | | | |
| ctc | ctc | ggg | cgg | gcc | ctc | ttc | ggg | aag | ccc | ctc | tcc | cca | agc | ctc | gcg | 480 |
| Leu | Leu | Gly | Arg | Ala | Leu | Phe | Gly | Lys | Pro | Leu | Ser | Pro | Ser | Leu | Ala | |
| 145 | | | | | 150 | | | | | 155 | | | | | 160 | |
| gag | cac | gcc | ctt | aag | gcc | ctg | gac | cgg | atc | atg | gcc | cag | acc | agg | agc | 528 |
| Glu | His | Ala | Leu | Lys | Ala | Leu | Asp | Arg | Ile | Met | Ala | Gln | Thr | Arg | Ser | |
| | | | | 165 | | | | | 170 | | | | | 175 | | |
| ccc | ctg | gcc | ctc | ctg | gac | ctg | gcc | gcc | gaa | gcc | cgc | ttc | cgg | aag | gac | 576 |
| Pro | Leu | Ala | Leu | Leu | Asp | Leu | Ala | Ala | Glu | Ala | Arg | Phe | Arg | Lys | Asp | |
| | | | 180 | | | | | 185 | | | | | 190 | | | |
| cgg | ggg | gcc | ctc | tac | cgc | gag | gcg | gaa | gcc | ctc | atc | gtc | cac | ccg | ccc | 624 |
| Arg | Gly | Ala | Leu | Tyr | Arg | Glu | Ala | Glu | Ala | Leu | Ile | Val | His | Pro | Pro | |
| | | 195 | | | | | 200 | | | | | 205 | | | | |
| ctc | tcc | cac | ctt | ccc | cga | gag | cgc | gcc | ctg | agc | gag | gcc | gtg | acc | ctc | 672 |
| Leu | Ser | His | Leu | Pro | Arg | Glu | Arg | Ala | Leu | Ser | Glu | Ala | Val | Thr | Leu | |
| | | 210 | | | | | 215 | | | | | 220 | | | | |
| ctg | gtg | gcg | ggc | cac | gag | acg | gtg | gcg | agc | gcc | ctc | acc | tgg | tcc | ttt | 720 |
| Leu | Val | Ala | Gly | His | Glu | Thr | Val | Ala | Ser | Ala | Leu | Thr | Trp | Ser | Phe | |
| 225 | | | | | 230 | | | | | 235 | | | | | 240 | |
| ctc | ctc | ctc | tcc | cac | cgc | ccg | gac | tgg | cag | aag | cgg | gtg | gcc | gag | agc | 768 |
| Leu | Leu | Leu | Ser | His | Arg | Pro | Asp | Trp | Gln | Lys | Arg | Val | Ala | Glu | Ser | |

```
                    245                 250                 255
gag gag gcg gcc ctc gcc gcc ttc cag gag gcc ctg agg ctc tac ccc        816
Glu Glu Ala Ala Leu Ala Ala Phe Gln Glu Ala Leu Arg Leu Tyr Pro
            260                 265                 270 ccc gcc tgg atc ctc acc cgg agg ctg gaa agg ccc ctc ctc ctg gga        864
Pro Ala Trp Ile Leu Thr Arg Arg Leu Glu Arg Pro Leu Leu Leu Gly
        275                 280                 285 gag gac cgg ctc ccc ccg ggc acc acc ctg gtc ctc tcc ccc tac gtg        912
Glu Asp Arg Leu Pro Pro Gly Thr Thr Leu Val Leu Ser Pro Tyr Val
    290                 295                 300 acc cag agg ctc cac ttc ccc gat ggg gag gcc ttc cgg ccc gag cgc        960
Thr Gln Arg Leu His Phe Pro Asp Gly Glu Ala Phe Arg Pro Glu Arg
305                 310                 315                 320 ttc ctg gag gaa agg ggg acc cct tcg ggg cgc tac ttc ccc ttt ggc        1008
Phe Leu Glu Glu Arg Gly Thr Pro Ser Gly Arg Tyr Phe Pro Phe Gly
                325                 330                 335 ctg ggg cag agg ctc tgc ctg ggg cgg gac ttc gcc ctc ctc gag ggc        1056
Leu Gly Gln Arg Leu Cys Leu Gly Arg Asp Phe Ala Leu Leu Glu Gly
            340                 345                 350 ccc atc gtc ctc agg gcc ttc ttc cgc cgc ttc cgc cta gac ccc ctc        1104
Pro Ile Val Leu Arg Ala Phe Phe Arg Arg Phe Arg Leu Asp Pro Leu
        355                 360                 365 ccc ttc ccc cgg gtc ctc gcc cag gtc acc ctg agg ccc gaa ggc ggg        1152
Pro Phe Pro Arg Val Leu Ala Gln Val Thr Leu Arg Pro Glu Gly Gly
    370                 375                 380 ctt ccc gcg cgg cct agg gag gag gtg cgg gcg tga                        1188
Leu Pro Ala Arg Pro Arg Glu Glu Val Arg Ala
385                 390                 395

<210> SEQ ID NO 4
<211> LENGTH: 395
<212> TYPE: PRT
<213> ORGANISM: Artificial sequence
<220> FEATURE:
<223> OTHER INFORMATION: Description of artificial sequence:N-terminal
      his tagged

<400> SEQUENCE: 4

Met His His His His His Lys Arg Leu Ser Leu Arg Glu Ala Trp
 1               5                  10                  15

Pro Tyr Leu Lys Asp Leu Gln Gln Asp Pro Leu Ala Val Leu Leu Ala
                20                  25                  30

Trp Gly Arg Ala His Pro Arg Leu Phe Leu Pro Leu Pro Arg Phe Pro
            35                  40                  45

Leu Ala Leu Ile Phe Asp Pro Glu Gly Val Glu Gly Ala Leu Leu Ala
        50                  55                  60

Glu Gly Thr Thr Lys Ala Thr Phe Gln Tyr Arg Ala Leu Ser Arg Leu
65                  70                  75                  80

Thr Gly Arg Gly Leu Leu Thr Asp Trp Gly Glu Ser Trp Lys Glu Ala
                85                  90                  95

Arg Lys Ala Leu Lys Asp Pro Phe Leu Pro Lys Asn Val Arg Gly Tyr
            100                 105                 110

Arg Glu Ala Met Glu Glu Glu Ala Arg Ala Phe Phe Gly Glu Trp Arg
        115                 120                 125

Gly Glu Glu Arg Asp Leu Asp His Glu Met Leu Ala Leu Ser Leu Arg
    130                 135                 140

Leu Leu Gly Arg Ala Leu Phe Gly Lys Pro Leu Ser Pro Ser Leu Ala
145                 150                 155                 160
```

```
Glu His Ala Leu Lys Ala Leu Asp Arg Ile Met Ala Gln Thr Arg Ser
            165                 170                 175

Pro Leu Ala Leu Leu Asp Leu Ala Ala Glu Ala Arg Phe Arg Lys Asp
            180                 185                 190

Arg Gly Ala Leu Tyr Arg Glu Ala Glu Ala Leu Ile Val His Pro Pro
            195                 200                 205

Leu Ser His Leu Pro Arg Glu Arg Ala Leu Ser Glu Ala Val Thr Leu
            210                 215                 220

Leu Val Ala Gly His Glu Thr Val Ala Ser Ala Leu Thr Trp Ser Phe
225                 230                 235                 240

Leu Leu Leu Ser His Arg Pro Asp Trp Gln Lys Arg Val Ala Glu Ser
            245                 250                 255

Glu Glu Ala Ala Leu Ala Ala Phe Gln Glu Ala Leu Arg Leu Tyr Pro
            260                 265                 270

Pro Ala Trp Ile Leu Thr Arg Arg Leu Glu Arg Pro Leu Leu Leu Gly
            275                 280                 285

Glu Asp Arg Leu Pro Pro Gly Thr Thr Leu Val Leu Ser Pro Tyr Val
            290                 295                 300

Thr Gln Arg Leu His Phe Pro Asp Gly Glu Ala Phe Arg Pro Glu Arg
305                 310                 315                 320

Phe Leu Glu Glu Arg Gly Thr Pro Ser Gly Arg Tyr Phe Pro Phe Gly
            325                 330                 335

Leu Gly Gln Arg Leu Cys Leu Gly Arg Asp Phe Ala Leu Leu Glu Gly
            340                 345                 350

Pro Ile Val Leu Arg Ala Phe Phe Arg Arg Phe Arg Leu Asp Pro Leu
            355                 360                 365

Pro Phe Pro Arg Val Leu Ala Gln Val Thr Leu Arg Pro Glu Gly Gly
            370                 375                 380

Leu Pro Ala Arg Pro Arg Glu Glu Val Arg Ala
385                 390                 395

<210> SEQ ID NO 5
<211> LENGTH: 1188
<212> TYPE: DNA
<213> ORGANISM: Artificial sequence
<220> FEATURE:
<221> NAME/KEY: misc_feature
<222> LOCATION: (1168)..(1185)
<223> OTHER INFORMATION: His tag
<220> FEATURE:
<223> OTHER INFORMATION: Description of artificial sequence:C-terminal
      His-tagged
<220> FEATURE:
<221> NAME/KEY: CDS
<222> LOCATION: (1)..(1188)

<400> SEQUENCE: 5 atg aag cgc ctt tcc ctg agg gag gcc tgg ccc tac ctg aaa gac ctc      48
Met Lys Arg Leu Ser Leu Arg Glu Ala Trp Pro Tyr Leu Lys Asp Leu
  1               5                  10                  15 cag caa gat ccc ctc gcc gtc ctg ctg gcg tgg ggc cgg gcc cac ccc      96
Gln Gln Asp Pro Leu Ala Val Leu Leu Ala Trp Gly Arg Ala His Pro
             20                  25                  30 cgg ctc ttc ctt ccc ctg ccc cgc ttc ccc ctg gcc ctg atc ttt gac     144
Arg Leu Phe Leu Pro Leu Pro Arg Phe Pro Leu Ala Leu Ile Phe Asp
         35                  40                  45 ccc gag ggg gtg gag ggg gcg ctc ctc gcc gag ggg acc acc aag gcc     192
Pro Glu Gly Val Glu Gly Ala Leu Leu Ala Glu Gly Thr Thr Lys Ala
     50                  55                  60
```

```
acc ttc cag tac cgg gcc ctc tcc cgc ctc acg ggg agg ggc ctc ctc      240
Thr Phe Gln Tyr Arg Ala Leu Ser Arg Leu Thr Gly Arg Gly Leu Leu
 65                  70                  75                  80 acc gac tgg ggg gaa agc tgg aag gag gcg cgc aag gcc ctc aaa gac      288
Thr Asp Trp Gly Glu Ser Trp Lys Glu Ala Arg Lys Ala Leu Lys Asp
                     85                  90                  95 ccc ttc ctg ccg aag aac gtc cgc ggc tac cgg gag gcc atg gag gag      336
Pro Phe Leu Pro Lys Asn Val Arg Gly Tyr Arg Glu Ala Met Glu Glu
                100                 105                 110 gag gcc cgg gcc ttc ttc ggg gag tgg cgg ggg gag gag cgg gac ctg      384
Glu Ala Arg Ala Phe Phe Gly Glu Trp Arg Gly Glu Glu Arg Asp Leu
            115                 120                 125 gac cac gag atg ctc gcc ctc tcc ctg cgc ctc ctc ggg cgg gcc ctc      432
Asp His Glu Met Leu Ala Leu Ser Leu Arg Leu Leu Gly Arg Ala Leu
    130                 135                 140 ttc ggg aag ccc ctc tcc cca agc ctc gcg gag cac gcc ctt aag gcc      480
Phe Gly Lys Pro Leu Ser Pro Ser Leu Ala Glu His Ala Leu Lys Ala
145                 150                 155                 160 ctg gac cgg atc atg gcc cag acc agg agc ccc ctg gcc ctc ctg gac      528
Leu Asp Arg Ile Met Ala Gln Thr Arg Ser Pro Leu Ala Leu Leu Asp
                    165                 170                 175 ctg gcc gcc gaa gcc cgc ttc cgg aag gac cgg ggg gcc ctc tac cgc      576
Leu Ala Ala Glu Ala Arg Phe Arg Lys Asp Arg Gly Ala Leu Tyr Arg
                180                 185                 190 gag gcg gaa gcc ctc atc gtc cac ccg ccc ctc tcc cac ctt ccc cga      624
Glu Ala Glu Ala Leu Ile Val His Pro Pro Leu Ser His Leu Pro Arg
            195                 200                 205 gag cgc gcc ctg agc gag gcc gtg acc ctc ctg gtg gcg ggc cac gag      672
Glu Arg Ala Leu Ser Glu Ala Val Thr Leu Leu Val Ala Gly His Glu
    210                 215                 220 acg gtg gcg agc gcc ctc acc tgg tcc ttt ctc ctc ctc tcc cac cgc      720
Thr Val Ala Ser Ala Leu Thr Trp Ser Phe Leu Leu Leu Ser His Arg
225                 230                 235                 240 ccg gac tgg cag aag cgg gtg gcc gag agc gag gag gcg gcc ctc gcc      768
Pro Asp Trp Gln Lys Arg Val Ala Glu Ser Glu Glu Ala Ala Leu Ala
                    245                 250                 255 gcc ttc cag gag gcc ctg agg ctc tac ccc ccc gcc tgg atc ctc acc      816
Ala Phe Gln Glu Ala Leu Arg Leu Tyr Pro Pro Ala Trp Ile Leu Thr
                260                 265                 270 cgg agg ctg gaa agg ccc ctc ctc ctg gga gag gac cgg ctc ccc ccg      864
Arg Arg Leu Glu Arg Pro Leu Leu Leu Gly Glu Asp Arg Leu Pro Pro
            275                 280                 285 ggc acc acc ctg gtc ctc tcc ccc tac gtg acc cag agg ctc cac ttc      912
Gly Thr Thr Leu Val Leu Ser Pro Tyr Val Thr Gln Arg Leu His Phe
    290                 295                 300 ccc gat ggg gag gcc ttc cgg ccc gag cgc ttc ctg gag gaa agg ggg      960
Pro Asp Gly Glu Ala Phe Arg Pro Glu Arg Phe Leu Glu Glu Arg Gly
305                 310                 315                 320 acc cct tcg ggg cgc tac ttc ccc ttt ggc ctg ggg cag agg ctc tgc     1008
Thr Pro Ser Gly Arg Tyr Phe Pro Phe Gly Leu Gly Gln Arg Leu Cys
                    325                 330                 335 ctg ggg cgg gac ttc gcc ctc ctc gag ggc ccc atc gtc ctc agg gcc     1056
Leu Gly Arg Asp Phe Ala Leu Leu Glu Gly Pro Ile Val Leu Arg Ala
                340                 345                 350 ttc ttc cgc cgc ttc cgc cta gac ccc ctc ccc ttc ccc cgg gtc ctc     1104
Phe Phe Arg Arg Phe Arg Leu Asp Pro Leu Pro Phe Pro Arg Val Leu
            355                 360                 365 gcc cag gtc acc ctg agg ccc gaa ggc ggg ctt ccc gcg cgg cct agg     1152
Ala Gln Val Thr Leu Arg Pro Glu Gly Gly Leu Pro Ala Arg Pro Arg
    370                 375                 380
```

```
gag gag gtg cgg gcg cat cac cat cat cat cac tga                    1188
Glu Glu Val Arg Ala His His His His His His
385                 390                 395

<210> SEQ ID NO 6
<211> LENGTH: 395
<212> TYPE: PRT
<213> ORGANISM: Artificial sequence
<220> FEATURE:
<223> OTHER INFORMATION: Description of artificial sequence:C-terminal
      His-tagged

<400> SEQUENCE: 6

Met Lys Arg Leu Ser Leu Arg Glu Ala Trp Pro Tyr Leu Lys Asp Leu
 1               5                  10                  15

Gln Gln Asp Pro Leu Ala Val Leu Leu Ala Trp Gly Arg Ala His Pro
             20                  25                  30

Arg Leu Phe Leu Pro Leu Pro Arg Phe Pro Leu Ala Leu Ile Phe Asp
         35                  40                  45

Pro Glu Gly Val Glu Gly Ala Leu Leu Ala Glu Gly Thr Thr Lys Ala
     50                  55                  60

Thr Phe Gln Tyr Arg Ala Leu Ser Arg Leu Thr Gly Arg Gly Leu Leu
 65                  70                  75                  80

Thr Asp Trp Gly Glu Ser Trp Lys Glu Ala Arg Lys Ala Leu Lys Asp
                 85                  90                  95

Pro Phe Leu Pro Lys Asn Val Arg Gly Tyr Arg Glu Ala Met Glu Glu
            100                 105                 110

Glu Ala Arg Ala Phe Phe Gly Glu Trp Arg Gly Glu Glu Arg Asp Leu
        115                 120                 125

Asp His Glu Met Leu Ala Leu Ser Leu Arg Leu Leu Gly Arg Ala Leu
    130                 135                 140

Phe Gly Lys Pro Leu Ser Pro Ser Leu Ala Glu His Ala Leu Lys Ala
145                 150                 155                 160

Leu Asp Arg Ile Met Ala Gln Thr Arg Ser Pro Leu Ala Leu Leu Asp
                165                 170                 175

Leu Ala Ala Glu Ala Arg Phe Arg Lys Asp Arg Gly Ala Leu Tyr Arg
            180                 185                 190

Glu Ala Glu Ala Leu Ile Val His Pro Pro Leu Ser His Leu Pro Arg
        195                 200                 205

Glu Arg Ala Leu Ser Glu Ala Val Thr Leu Leu Val Ala Gly His Glu
    210                 215                 220

Thr Val Ala Ser Ala Leu Thr Trp Ser Phe Leu Leu Leu Ser His Arg
225                 230                 235                 240

Pro Asp Trp Gln Lys Arg Val Ala Glu Ser Glu Ala Ala Leu Ala
                245                 250                 255

Ala Phe Gln Glu Ala Leu Arg Leu Tyr Pro Pro Ala Trp Ile Leu Thr
            260                 265                 270

Arg Arg Leu Glu Arg Pro Leu Leu Leu Gly Glu Asp Arg Leu Pro Pro
        275                 280                 285

Gly Thr Thr Leu Val Leu Ser Pro Tyr Val Thr Gln Arg Leu His Phe
    290                 295                 300

Pro Asp Gly Glu Ala Phe Arg Pro Glu Arg Phe Leu Glu Arg Gly
305                 310                 315                 320

Thr Pro Ser Gly Arg Tyr Phe Pro Phe Gly Leu Gly Gln Arg Leu Cys
                325                 330                 335
```

```
Leu Gly Arg Asp Phe Ala Leu Leu Glu Gly Pro Ile Val Leu Arg Ala
            340                 345                 350

Phe Phe Arg Arg Phe Arg Leu Asp Pro Leu Pro Phe Pro Arg Val Leu
        355                 360                 365

Ala Gln Val Thr Leu Arg Pro Glu Gly Gly Leu Pro Ala Arg Pro Arg
    370                 375                 380

Glu Glu Val Arg Ala His His His His His His
385                 390                 395

<210> SEQ ID NO 7
<211> LENGTH: 30
<212> TYPE: DNA
<213> ORGANISM: Artificial sequence
<220> FEATURE:
<223> OTHER INFORMATION: Description of artificial sequence:PCR-Primer

<400> SEQUENCE: 7
cgaagctcat atgaagcgcc tttccctgag                                              30

<210> SEQ ID NO 8
<211> LENGTH: 30
<212> TYPE: DNA
<213> ORGANISM: Artificial sequence
<220> FEATURE:
<223> OTHER INFORMATION: Description of artificial sequence:PCR-Primer

<400> SEQUENCE: 8
gcgaattcac gcccgcacct cctccctagg                                              30

<210> SEQ ID NO 9
<211> LENGTH: 42
<212> TYPE: DNA
<213> ORGANISM: Artificial sequence
<220> FEATURE:
<223> OTHER INFORMATION: Description of artificial sequence:PCR-Primer

<400> SEQUENCE: 9
cgaagctcat atgcatcacc atcatcatca caagcgcctt tc                                42

<210> SEQ ID NO 10
<211> LENGTH: 42
<212> TYPE: DNA
<213> ORGANISM: Artificial sequence
<220> FEATURE:
<223> OTHER INFORMATION: Description of artificial sequence:PCR-Primer

<400> SEQUENCE: 10
cggaattcag tgatgatgat ggtgatgcgc ccgcacctcc tc                                42

<210> SEQ ID NO 11
<211> LENGTH: 471
<212> TYPE: PRT
<213> ORGANISM: Bacillus megaterium

<400> SEQUENCE: 11

Thr Ile Lys Glu Met Pro Gln Pro Lys Thr Phe Gly Glu Leu Lys Asn
                5                   10                  15

Leu Pro Leu Leu Asn Thr Asp Lys Pro Val Gln Ala Leu Met Lys Ala
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60
```

```
Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Ile
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg
465                 470
```